(12) United States Patent
Kelly et al.

(10) Patent No.: US 6,242,448 B1
(45) Date of Patent: Jun. 5, 2001

(54) TRISUBSTITUTED-OXAZOLE DERIVATIVES AS SEROTONIN LIGANDS

(75) Inventors: Michael Gerard Kelly, Newbury Park, CA (US); Lynne Padilla Greenblatt, Lambertville; Frances Christy Nelson, Wyckoff, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/459,800

(22) Filed: Dec. 13, 1999

Related U.S. Application Data

(60) Provisional application No. 60/135,115, filed on Dec. 17, 1998.

(51) Int. Cl.$^7$ ..................... A61K 31/495; C07D 413/00; C07D 214/04
(52) U.S. Cl. ..................... 514/254.02; 544/369; 544/392
(58) Field of Search ..................... 514/254.02; 544/369, 544/392

(56) References Cited

FOREIGN PATENT DOCUMENTS

| | | |
|---|---|---|
| 704839 | 7/1995 | (AU). |
| WO9109857 | 7/1991 | (WO). |
| WO9407489 | 4/1994 | (WO). |
| 9938864 | * 8/1999 | (WO). |

* cited by examiner

*Primary Examiner*—Mukund J. Shah
*Assistant Examiner*—Sudhaker B. Patel
(74) *Attorney, Agent, or Firm*—Rebecca R. Barrett

(57) ABSTRACT

Compounds of the formula

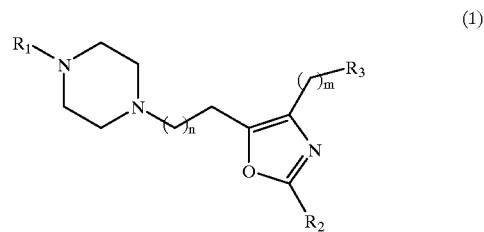

(1)

are useful for the treatment of anxiety, depression and related CNS disorders and other conditions such as the treatment of alcohol and drug withdrawal, sexual dysfunction and Alzheimer's disease.

26 Claims, No Drawings

TRISUBSTITUTED-OXAZOLE DERIVATIVES AS SEROTONIN LIGANDS

This application claims the benefit of U.S. Provisional application No. 60/135,115 filed Dec. 17, 1998.

BACKGROUND OF THE INVENTION

WO 9109857 (Sanofi SA) describes aminosubstituted heterocycles that are antagonists of platelet activating factor. WO 9407489 (Salt Inst.) describes the (heteroaryl-alkyl) piperazine compounds to inhibit neuronal nicotinic acetyl choline receptors e.g. to treat hypertension of nicotine addiction. DE 4425146 (BASF) describes heteroaryl and aryl substituted (heteroaryl-alkyl)-piperazine compounds as selective dopamine D3 receptor ligands.

DESCRIPTION OF THE INVENTION

This invention relates to novel 4-(arylpiperazin-1-yl) oxazole derivatives which are agonists and antagonists of the 5HT1A receptor subtype. By virtue of their high binding affinity to the 5HT1A receptor, compounds of the present invention are useful for the treatment of central nervous system (CNS) disorders such as depression, anxiety, panic, OCD, sleep disorders, sexual dysfunction, alcohol and drug addiction, cognition enhancement, Alzheimer's disease, Parkinson's disease, obesity and migraine.

Compounds of the present invention are represented by the general formula (1),

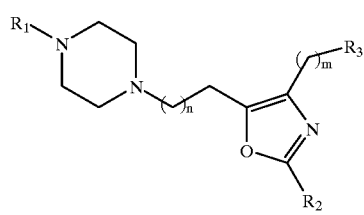

(1)

in which:
R$_1$ is aryl or heteroaryl;
R$_2$ is alkyl, alkylcycloalkyl, cycloalkyl, aryl, alkylaryl, heteroaryl, alkylheteroaryl, heterocycloalkyl, or alkyl-heterocycloalkyl; provided that the point of attachment is a carbon atom;
R3 is alkyl, alkylcycloalkyl, cycloalkyl, aryl, alkylaryl, heteroaryl, alkylheteroaryl, heterocycloalkyl or alkyl-heterocycloalkyl; n is 0 or 1 and m is an integer from 1 to 3; or a pharmaceutical salt thereof.

"Alkyl", whether used alone or as part of a group such as "alkoxy", means a branched or straight chain having from 1 to 6 carbon atoms. Exemplary alkyl groups include methyl, ethyl, propyl, isopropyl, butyl, isobutyl, t-butyl, pentyl and hexyl. Lower alkyl refers to alkyl having from 1 to 6 carbon atoms. The alkyl may be substituted with one or more substituents.

"Aryl" whether used alone or as part of a group such as "aralkyl", means mono or bicyclic aromatic ring having from 6 to 10 carbon atoms. Monocyclic rings preferably have 6 members and bicyclic rings preferably have 8, 9 or 10 membered ring structures. Preferred aryl groups are phenyl, 1-naphthyl and 2-naphthyl. The aryl may be substituted with one to three substituents.

"Heteroaryl" whether used alone or as part of a group such as "heteroaralkyl", means 5 to 10 membered mono or bicyclic aromatic ring having from 1 to 3 heteroatoms selected from N, O and S. Monocyclic rings preferably have 5 or 6 members and bicyclic rings preferably have 8, 9 or 10 membered ring structures. Exemplary heteroaryls include pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl, benzopyranyl and benzodioxanyl. Preferred heteroaryl groups include pyridyl, furyl, thienyl, quinolyl, isoquinolyl, indolyl, benzodioxanyl and benzopyranyl. Still more preferred heteroaryls include 1,4-benzodioxan-5-yl and benzopyranyl The heteroaryl may also be substituted with one to 3 substituents.

"Cycloalkyl" means a cyclic alkyl of 3 to 8 carbon atoms. Exemplary cycloalkyl groups include cyclopentyl and cyclohexyl. The cycloalkyl group may be substituted with 1 to 3 substituents.

"Heterocycloalkyl" means a cyclic alkyl of 3 to 8 member having 1 to 3 heteroatoms selected from N, O and S. The heterocycloalkyl group may be substituted with 1 to 3 substituents.

"Alkoxy" means an alkyl-O group in which the alkyl group is as previously described. Exemplary alkoxy groups include methoxy, ethoxy, n-propoxy, i-propoxy, n-butoxy, and t-butoxy. The cycloalkyl may bs substituted with 1 to 3 substituents.

"Halogen" includes fluorine, chlorine, iodine and bromine.

Suitable substituents include, unless otherwise noted, halogen, alkyl, hydroxy, alkoxy, amino, amido, nitro, alkylamino, alkylamido, perhaloalkyl, carboxyalkyl, carboxy, carbamide, dialkylamino and aryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl is an alkyl-cycloalkyl group in which alkyl and cycloalkyl are as previously described.

It is understood that the definition of compounds of Formula (1) include racemates, racemic mixtures, and individual enantiomers and diastereomers. All asymmetric forms, individual isomers and combinations thereof are within the scope of the present invention.

Optically active isomers may be prepared, for example, by resolving the racemic mixtures. The resolution can be carried out by methods known to those skilled in the art such as in the presence of resolving agent, by chromatography, or combinations thereof.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

Compounds of the present invention may be prepared using conventional methods, utilizing for example the disconnections A and B shown in Scheme 1 below.

Scheme 1

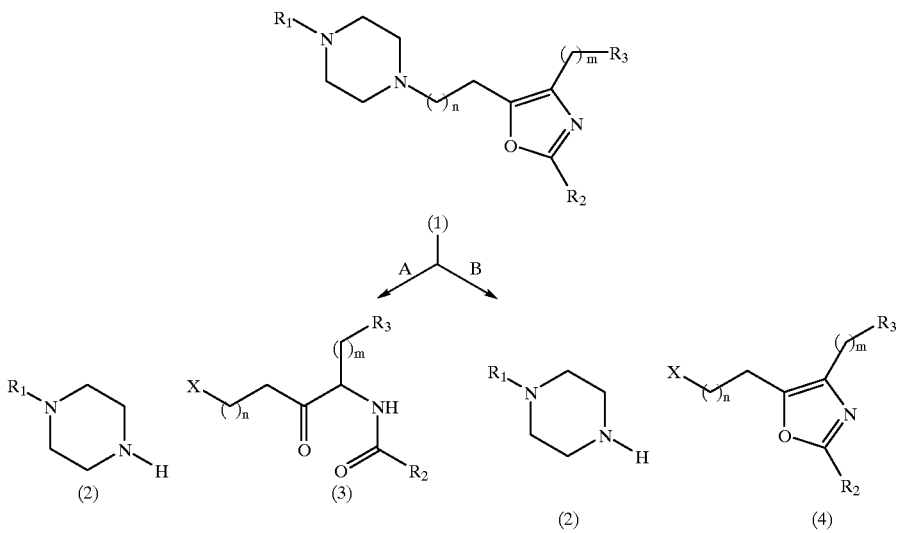

Aryl piperazines (2) are either commercially available or readily prepared by those skilled in the art of organic synthesis, for example by the reaction of an aniline ($R_1NH_2$,) with bis(2-chloroethyl)amine.

In path A, the amidoalkyl chloride of formula (3) (X=Cl, n=0) may be prepared from the corresponding amine (5) using standard acylating conditions known to those skilled in the art of organic synthesis.

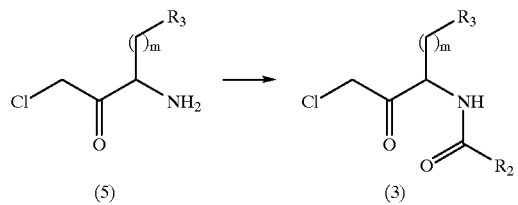

The alkyl chloride (5) is readily available, and may be prepared from the corresponding protected amino acid (6) using, for example, the Arndt-Eistert reaction. For example, reaction of the acid chloride of (6) with diazomethane and treatment of the resulting α-diazoketone (7) with HCl affords the required product

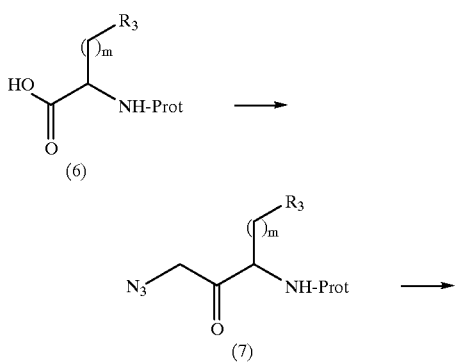

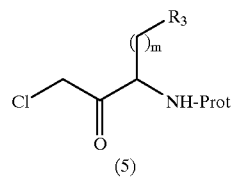

Reaction of (2) with an alkyl chloride (3) affords the ketoamide (8). This product can be cyclized to the desired oxazole (1) by the action of a dehydrating agent such as the chlorinating agent POCl3.

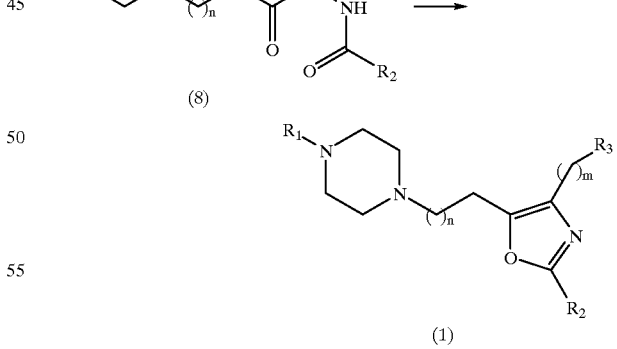

In path B, the chloroalkyloxazole (4) (X=Cl, n=0 or 1) may be prepared from the ketoamide (3) by the action of a dehydrating agent such as POCl3. The subsequent alkylation of an arylpiperazine (2) with the chloroalkyloxazole (4) may be conducted in a suitable solvent (e.g. acetone), optionally utilizing a base (e.g. potassium carbonate or triethylamine) as an acid scavenger.

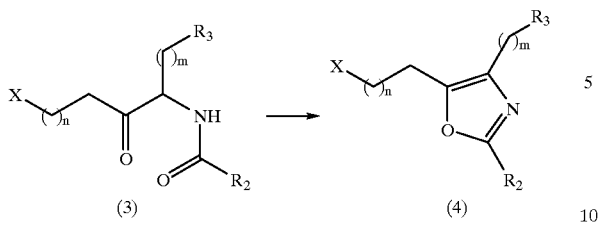

Alternatively, the chloroalkyloxazole (4) (X=Cl, n=0) can be homologated to the nitrile (11) by the action of sodium cyanide, which can provide the carboxylic acid (9) upon acid or base mediated hydrolysis.

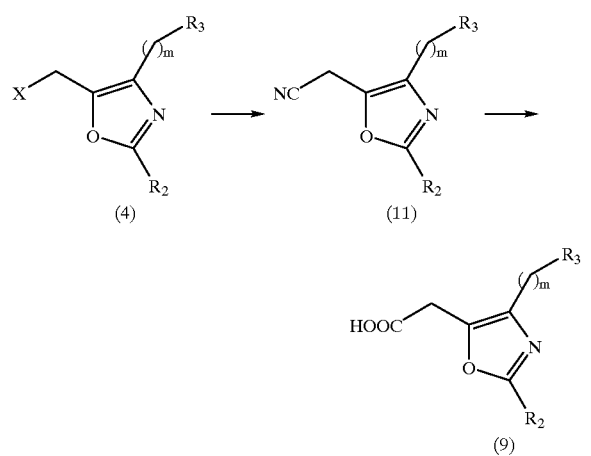

Derivatives of the 2,4-disubstituted oxazole-5-acetic acid (9) can also be prepared by alternative routes. Such methods are known, and have been described, for example by Dow R. L., *J. Org. Chem.*, (1990), 55(1), 386–8. Condensation of the acid (a) with the piperazine (2) affords the amide (10) which can be reduced to the required product using a hydride reducing agent such as lithium aluminium hydride or borane.

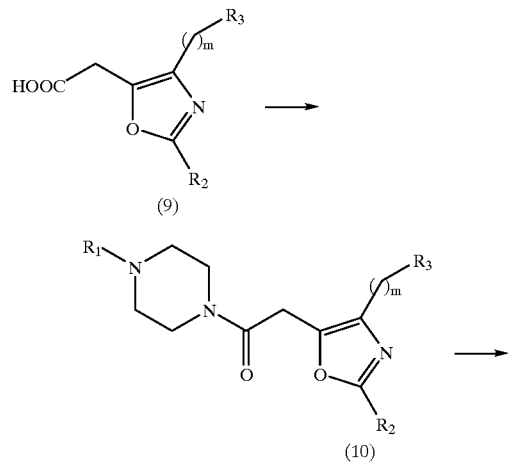

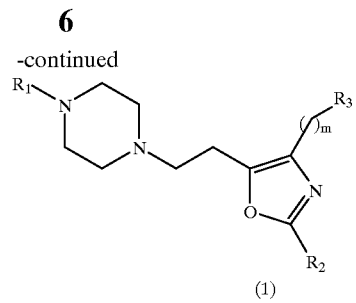

The following non-limiting specific examples are included to illustrate the synthetic procedures used for preparing compounds of the formula 1. In these examples, all chemicals and intermediates are either commercially available or can be prepared by standard procedures found in the literature or are known to those skilled in the art of organic synthesis. Several preferred embodiments are described to illustrate the invention. However, it should be understood that the invention is not intended to be limited to the specific embodiments.

EXAMPLE 1

N-Cyclohexanoyl-L-Phenylalanylchloromethylketone

A cooled (−10° C.) mixture containing L-phenylalanylchloromethylketone (3.2 mmole) in CH2Cl2 (30 ml) and potassium carbonate (10 mmole) in water (10 ml) was treated with cyclohexanecarbonylchloride (3.2 mmole). The resulting mixture was stirred for two hours at ambient temperature. The organic layer was separated, washed with water (3×20 ml) and dried over anhydrous magnesium sulfate. Filtration and concentration in vacuo gave the titled compound as a cream colored solid (2.6 mmole, 81%).

Elemental Analysis for: C17H22C1NO2 Calculated: C, 66.33; H, 7.20; N, 4.55 Found: C, 66.12; H, 7.12; N, 4.34

EXAMPLE 2

4-Benzyl-5-chloromethyl-2-cyclohexyloxazole

Under a nitrogen atmosphere, a benzene solution (26 ml) of the chloromethylketone (2.6 mmole) from example 1 was treated with dimethylformamide (2 ml) and phosphorus oxychloride (26 mmole). The mixture was heated to reflux for 15 minutes while water was collected in a Dean-Stark apparatus. After cooling to room temperature, the reaction mixture was poured onto ice (25 g), the solution made basic with sodium bicarbonate and the product was extracted with ethyl acetate (2×30 ml). The combined organics were washed with water (2×30 ml), dried over anhydrous magnesium sulfate, filtered and concentrated in vacuo to afford the crude product. This was purified by silica-gel flash chromatography, eluting with dichloromethane, to afford the titled product as a light yellow oil (1.03 mmole, 40%).

Elemental Analysis for: C17H20C1NO Calculated: C, 70.46; H, 6.96; N, 4.83 Found: C, 70.35; H, 7.12; N, 5.02

EXAMPLE 3

N-Pivaloyl-L-Phenylalanylchloromethylketone

The titled compound was isolated in 80% yield when pivaloyl chloride (5 mmole) was used in the procedure outlined in example 1 above.

Elemental Analysis for: C15H20C1NO2 Calculated: C, 63.94; H, 7.15; N, 4.97 Found: C, 64.23; H, 7.27; N, 5.12

EXAMPLE 4

4-Benzyl-5-chloromethyl-2-tertbutyloxazole

The title compound was prepared using N-pivolyl-L-phenylalanylchloromethyl ketone (4 mmole) in the procedure described in example 2. The product was obtained as a light yellow oil (2.24 mmole, 56% yield) after SiO2 "flash" Chromatography.

Elemental Analysis for: C15H18C1NO Calculated: C, 68.30; H, 6.88; N, 5.31 Found: C, 68.52; H, 7.02; N, 5.42

EXAMPLE 5

N-Benzyl-L-Phenylalanylchloromethylketone

The titled compound was prepared in 88% yield by substituting benzoyl chloride (5 mmole) into the procedure outlined in example 1 above. The product (4.4 mmole) was obtained as a yellow oil, and was used without further purification.

Elemental Analysis for: C17H16C1NO2 Calculated: C, 67.66; H, 5.34; N, 4.64 Found: C. 67.55; H, 5.30; N, 4.54

EXAMPLE 6

4-Benzyl-5-chloromethyl-2-phenyloxazole

The title compound was prepared using N-benzoyl-L-phenylalanylchloromethylketone (4.4 mmole) in the procedure described in example 2. The product was obtained as a light yellow oil (1.4 mmole, 32% yield) after SiO2 "flash" Chromatography.

Elemental Analysis for: C17H14C1NO Calculated: C, 71.96; H, 4.97; N, 4.94 Found: C, 72.25; H, 5.15; N, 5.23

EXAMPLE 7

N-Cyclohexaneacetyl-L-Phenylalanylchloromethylketone

The compound was prepared in 83% yield by substituting cyclohexylacetyl chloride (3 mmole) into the procedure outlined in example 1 above. This provided the titled compound as a light yellow oil (2.5 mmole) which was used without further purification.

Elemental Analysis for: C18H24C1NO2 Calculated: C, 67.17; H, 7.52; N, 4.35 Found: C, 67.35; H, 7.50; N, 4.51

EXAMPLE 8

4-Benzyl-5-chloromethyl-2-cyclohexylmethyloxazole

The title compound was prepared using N-cyclohexaneacetyl-L-phenylalanylchloromethyl ketone (2.5 mmole) in the procedure described in example 2. The product was obtained as a light yellow oil (1.2 mmole, 48% yield) after SiO2 "flash" Chromatography.

Elemental Analysis for: C18H22C1NO Calculated: C, 71.16; H, 7.30; N, 4.61 Found: C,71.23; H,7.45;N,4.65

EXAMPLE 9

1-(4-Benzyl-2-cyclohexyl-oxazol-5-ylmethyl)-4(2,3-dihydro-benzo[1,4]dioxin-5-yl)-piperazine A suspension of 1-(2,3-dihydro-1,4-benzodioxan-5-yl) piperazine (0.88 mmole), potassium carbonate (2.16 mmole), potassium iodide (0.5 mmole) and 4-benzyl-5-chloro methyl-2-cyclohexyloxazole (0.88 mmole) from example 2, in acetone (10 ml), was stirred at ambient temperature for three days. The solvent was removed in vacuo, water (50 ml) added and the product extracted into ethyl acetate (3×50 ml). The combined organics were washed with water (50 ml), dried over anhydrous sodium sulfate, filtered and concentrated in vacuo and the product purified by "flash" chromatography over silica gel to afford a colorless oil (63% yield). An ethanolic solution of the product was treated with 2 equivalents of 1N-HCl in diethyl ether to afford the HCl salt of the titled compound as a white solid.

mp 211° C. (Dec.)

Elemental Analysis for: C29H35N3O3 2HCl Calculated: C, 63.73; H, 6.82; N, 7.69 Found: C, 63.40; H, 6.87; N, 7.51

EXAMPLE 10

4-[4-(4-Benzyl-2-cyclohexyl-oxazol-5-ylmethyl)-piperazin-1-yl]-1H-indole

A mixture containing 4-piperazinoindole (0.2 mmole), potassium carbonate (0.5 mmole), potassium iodide (0.08 mmole) and 4-benzyl-5-chloromethyl-2-cyclohexyl oxazole (0.19 mmole) from example 2 was stirred in acetone (2 ml) for 16 hr. The mixture was concentrated in vacuo, water (10 ml) added, and the product extracted into dichloromethane (2×10 ml). The combined organics was washed with water (5 ml), dried over anhydrous magnesium sulfate, filtered and concentrated in vacuo to afford the required product as a beige solid (94% yield). An ethanolic solution (5 ml) of the product was treated with fumaric acid (1 equivalent), and the resulting salt crystallized from diethyl ether to afford the titled product as a light beige powder.

mp 163–163° C.

Elemental Analysis for: C29H34N4O 1.0C4H4O4 1.0 H2O Calculated: C, 67.33; H, 6.85; N, 9.52 Found: C, 67.51; H, 6.48; N, 9.36

EXAMPLE 11

1-(4Benzyl-2-cyclohexyl-oxazol-5-ylmethyl)-4-(2-methoxyphenyl)-piperazine

Under a N2 atmosphere, an acetone (20 ml) suspension of 2-methoxyphenylpiperazine (2 mmole), potassium carbonate (4 mmole), potassium iodide (0.4 mmole) and N-cyclohexanoyl-L-phenylalanylchloromethyl ketone (2 mmole) from example 1, was stirred at room temperature for 16 hr. The solvent was removed in vacuo, water (50 ml) added, and the product extracted into ethyl acetate (3×30 ml). The combined organics were washed with water (30 ml), brine (30 ml) and dried over anhydrous sodium sulfate. Filtration and concentration in vacuo afforded the required ketoamide as a yellow oil (1.86 mmole, 93% yield). The product was dissolved in POC13 (25 ml), DMF (0.5 ml) added and the mixture stirred at 60° C. for 2 hr. The solvent was removed in vacuo, water (30 ml) added, and the resulting solution made basic by the addition of NaOH. The product was extracted into ethyl acetate (3×30 ml), and the combined organics washed with water (30 ml), brine (30 ml) and dried over anhydrous magnesium sulfate. Filtration and concentration in vacuo gave a brown oil (1.3 mmole, 74% yield). The crude product was purified by "flash" chromatography over silica-gel to afford the titled compound as a light yellow oil (0.77 mmole, 40% yield). This was transformed into its mono-fumarate salt, a white crystalline powder, using the procedure outlined in example 10 above.

mp 164–166° C.

Elemental Analysis for: C28H35N3O2 1.0C4H4O4 1.0 H2O Calculated: C, 66.30; H, 7.13; N, 7.25 Found: C, 65.96; H, 6.73; N, 6.71

EXAMPLE 12

1-(4-Benzyl-2-tert-butyl-oxazol-5-ylmethyl)-4-(2-methoxyphenyl)-piperazine

A suspension containing 2-methoxyphenylpiperazine (1.0 mmole), potassium carbonate (2.0 mmole), potassium iodide (0.5 mmole) and 4-benzyl-5-chloromethyl-2-tertbutyl oxazole (1.0 mmole) from example 4, was stirred in acetone (10 ml) at ambient temperature for three days. The solvent was removed in vacuo, water (50 ml) added and the product extracted into ethyl acetate (3×50 ml). The combined organics were washed with water (50 ml), dried over anhydrous sodium sulfate, filtered and concentrated in vacuo. The product was purified by "flash" chromatography over silica gel to afford the titled compound as a colorless oil (0.64 mmole, 64% yield). This was transformed into its mono-fumarate salt, a white crystalline powder, using the procedure outlined in example 10 above.

mp 155–156° C.

Elemental Analysis for: C26H33N3O3 1.0C4H4O4 Calculated: C, 67.27; H, 6.98; N, 7.84 Found: C, 67.08; H, 6.59; N, 7.88

EXAMPLE 13

4-[4-(4-Benzyl-2-tert-butyl-oxazol-5-ylmethyl)-piperazin-1-yl]-1H-indole

A suspension containing 4-indolylpiperazine (1.5 mmole), potassium carbonate (3.0 mmole), potassium iodide (0.75 mmole) and 4-benzyl-5-chloromethyl-2-tertbutyl oxazole (1.5 mmole) from example 4, was stirred in acetone (15 ml) at ambient temperature for 16 hr. The solvent was removed in vacuo, water (50 ml) added and the product extracted into ethyl acetate (3×50 ml). The combined organics were washed with water (50 ml), dried over anhydrous sodium sulfate, filtered and concentrated n vacuo and the product purified by "flash" chromatography over silica gel to afford the titled compound as an off-white crystalline powder (1.1 mmole, 73% yield). mp 160–161° C.

Elemental Analysis for: C27H32N4O Calculated: C, 75.67; H, 7.53; N, 13.07 Found: C, 75.97; H, 7.72; N, 12.95

EXAMPLE 14

1-(4-Benzyl-2-tert-butyl-oxazol-5-ylmethyl)-4-(2.3-dihydro-benzo[1,4]dioxin-5-yl)-piperazine A suspension containing 1-(2,3-dihydro-1,4-benzodioxan-5-yl)piperazine (0.64 mmole), potassium carbonate (1.6 mmole), potassium iodide (0.64 mmole) and 4-benzyl-5-chloromethyl-2-tertbutyloxazole (0.64 mmole) from example 4, in acetone (10 ml), was stirred at ambient temperature for three days. The solvent was removed in vacuo, water (50 ml) added and the product extracted into ethyl acetate (3×50 ml). The combined organics were washed with water (50 ml), dried over anhydrous sodium sulfate, filtered and concentrated in vacuo and the product purified by "flash" chromatography over silica gel to afford a colorless oil (0.34 mmole, 53% yield). An ethyl acetate solution (10 ml) of the product was treated with 2 equivalents of IN-HCl in diethyl ether to afford the HCl salt of the titled compound as a white solid.

mp 211° C. (Dec.)

Elemental Analysis for: C27H33N3O3 2HCl Calculated: C, 62.31; H, 6.78; N, 8.07 Found: C, 61.85; H, 6.92; N, 8.12

EXAMPLE 15

1-(4-Benzyl-2-cyclohexylmethyl-oxazol-5-ylmethyl)-4-(2-methoxyphenyl)-piperazine A suspension containing 2-methoxyphenylpiperazine (2.0 mmole), potassium carbonate (4.0 mmole), potassium iodide (1.0 mmole) and 4-benzyl-5-chloromethyl-2-cyclohexylmethyl oxazole (2.0 mmole) from example 8, was stirred in acetone (20 ml) at ambient temperature for 18 hr. The solvent was removed in vacuo, water (50 ml) added and the product extracted into ethyl acetate (3×50 ml). The combined organics were washed with water (50 ml), dried over anhydrous sodium sulfate, filtered and concentrated in vacuo. The product was purified by "flash" chromatography over silica gel to afford the titled compound as an off-white crystalline powder (1.62 mmole, 81% yield). This was transformed into its mono-fumarate salt, an off-white crystalline powder, using the procedure outlined in example 10 above.

mp 133–134° C.

Elemental Analysis for: C29H37N3O2 1.0C4H4O4 Calculated: C, 68.85; H, 7.18; N, 7.30 Found: C, 68.43; H, 7.20; N, 7.17

EXAMPLE 16

4-[4-(4-Benzyl-2-cyclohexylmethyl-oxazol-5-yl methyl)-piperazin-1-yl]-1H-indole

A suspension containing 4-indolylpiperazine (1.0 mmole), potassium carbonate (2.0 mmole), potassium iodide (0.5 mmole) and 4-benzyl-5-chloromethyl-2-cyclohexylmethyl oxazole (1.0 mmole) from example 8, was stirred in acetone (15 ml) at ambient temperature for 16 hr. The solvent was removed in vacuo, water (50 ml) added and the product extracted into ethyl acetate (2×50 ml). The combined organics were washed with water (40 ml), dried over anhydrous sodium sulfate, filtered and concentrated in vacuo. The product was purified by "flash" chromatography over silica gel to afford the titled compound as an off-white crystalline powder (0.82 mmole, 82% yield). This was transformed into its mono-fumarate salt, an off-white crystalline powder, using the procedure outlined in example 10 above.

mp 189–190° C.

Elemental Analysis for: C30H36N4O 1.0C4H4O4 Calculated: C, 69.84; H, 6.90; N, 9.58 Found: C, 69.37; H, 6.93; N, 9.34

EXAMPLE 17

1-(4-Benzyl-2-phenyl-oxazol-5-ylmethyl)-4-(2-methoxyphenyl)-piperazine

A suspension containing 2-methoxyphenylpiperazine (1.0 mmole), potassium carbonate (2.0 mmole), potassium iodide (0.5 mmole) and 4-benzyl-5-chloromethyl-2-phenyloxazole (1.0 mmole) from example 6, was stirred in acetone (15 ml) at ambient temperature for 16 hr. The solvent was removed in vacuo, water (50 ml) added and the product extracted into ethyl acetate (2×50 ml). The combined organics were washed with water (40 ml), brine (40 ml), dried over anhydrous sodium sulfate, filtered and concentrated in vacuo. The product was purified by "flash" chromatography over silica gel to afford the titled compound as an off-white crystalline powder (0.74 mmole, 74% yield). This was transformed into its mono-fumarate salt, an off-white crystalline powder, using the procedure outlined in example 10 above. mp 175–175° C.

Elemental Analysis for: C28H29N3O2 1.0C4H4O4 Calculated: C, 69.17; H, 5.99; N, 7.56 Found: C, 68.85; H, 6.09; N, 7.48

EXAMPLE 18

1-(2-Cyclohexyl-4{(2-naphthyl)methyl}-oxazol-5-ylmethyl)-4-

(2-methoxyphenyl)-piperazine

Under a N2 atmosphere, an acetone (20 ml) suspension of 2-methoxyphenylpiperazine (2 mmole), potassium carbonate (4 mmole), potassium iodide (0.5 mmole) and N-cyclohexanoyl-β-(2-naphthyl)-alanyl-chloromethylketone (2 mmole) (prepared according to example 1), was stirred at room temperature for 16 hr. The solvent was removed in vacuo, water (50 ml) added, and the product extracted into ethyl acetate (3×30 ml). The combined organics were washed with water (30 ml), brine (30 ml) and dried over anhydrous sodium sulfate. Filtration and concentration in vacuo afforded the required ketoamide as a yellow oil (1.78 mmole, 89% yield). The product was dissolved in POC13 (25 ml), DMF (0.5 ml) added and the mixture stirred at 60° C. for 2.5 hr. The solvent was removed in vacuo, water (30 ml) added, and the resulting solution made basic by the addition of 1N-NaOH. The product was extracted into ethyl acetate (3×35 ml), and the combined organics washed with water (30 ml), brine (30 ml) and dried over anhydrous magnesium sulfate. Filtration and concentration in vacuo gave a brown oil (1.2 mmole, 67% yield). The crude product was purified by "flash" chromatography over silica-gel to afford the titled compound as a light yellow oil (0.64 mmole, 53% yield). This was transformed into its mono-fumarate salt, a white crystalline powder, using the procedure outlined in example 10 above.

Elemental Analysis for: C32H37N3O2 1.0C4H4O4 Calculated: C, 70.68; H, 6.76; N, 6.87 Found: C, 70.42; H, 6.70; N, 6.79

EXAMPLE 19

1-(2-Cyclohexyl-4-(4-fluorobenzyl)-oxazol-5-ylmethyl)-4-

(2-methoxyphenyl)-piperazine

Under a N2 atmosphere, an acetone (15 ml) suspension of 2-methoxyphenylpiperazine (1.5 mmole), potassium carbonate (3 mmole), potassium iodide (0.4 mmole) and N-cyclohexanoyl-p-fluorophenylalanyl-chloromethylketone (1.5 mmole) (prepared according to example 1), was stirred at room temperature for 18 hr. The solvent was removed in vacuo, water (50 ml) added, and the product extracted into ethyl acetate (3×25 ml). The combined organics were washed with water (30 ml), brine (30 ml) and dried over anhydrous sodium sulfate. Filtration and concentration in vacuo afforded the required ketoamide as a light yellow oil (1.25 mmole, 83% yield). The product was dissolved in POC13 (25 ml), DMF (0.5 ml) added and the mixture stirred at 60° C. for 2 hr. The solvent was removed in vacuo, water (30 ml) added, and the resulting solution made basic by the addition of 1N-NaOH. The product was extracted into ethyl acetate (3×35 ml), and the combined organics washed with water (30 ml), brine (30 ml) and dried over anhydrous magnesium sulfate. Filtration and concentration in vacuo gave a brown oil which was purified by "flash" chromatography over silica-gel to afford the titled compound as a light yellow oil (0.44 mmole, 35% yield). This was transformed into its mono-fumarate salt, a white crystalline powder, using the procedure outlined in example 10 above.

Elemental Analysis for: C28H34FN3O2 1.0C4H4O4 Calculated: C, 66.31; H, 6.61; N, 7.25 Found: C, 66.63; H, 6.70; N, 7.45

EXAMPLE 20

1-(4-Benzyl-2-cyclohexylmethyl-oxazol-5-ylmethyl)-4-(2-fluorophenyl)-piperazine

A suspension containing 2-fluorophenylpiperazine (2.0 mmole), potassium carbonate (4.0 mmole), potassium iodide (1.0 mmole) and 4-benzyl-5-chloromethyl-2-cyclohexylmethyl oxazole (2.0 mmole) from example 8, was stirred in acetone (20 ml) at ambient temperature for 18 hr. The solvent was removed in vacuo, water (50 ml) added and the product extracted into ethyl acetate (3×50 ml). The combined organics were washed with water (50 ml), dried over anhydrous sodium sulfate, filtered and concentrated in vacuo. The product was purified by "flash" chromatography over silica gel to afford the titled compound as an off-white crystalline powder (1.3 mmole, 65% yield). An ethyl acetate solution (10 ml) of the product was treated with 2 equivalents of ethereal 1N-HCl to afford the HCl salt of the titled compound as a white solid.

Elemental Analysis for: C28H34FN3O 2.0HCl Calculated: C, 64.61; H, 6.97; N, 8.07 Found: C, 64.55; H, 7.11; N, 8.17

EXAMPLE 21

1-(4-Benzyl-2-cyclohexyl-oxazol-5-ylmethyl)-

4-(2-pyrimidyl)-piperazine

A suspension of 1-(2-pyrimidyl)piperazine (1.4 mmole), potassium carbonate (2.8 mmole), potassium iodide (0.5 mmole) and 4-benzyl-5-chloromethyl-2-cyclohexyloxazole (1.4 mmole) from example 2, in acetone (15 ml), was stirred at ambient temperature for 18 hr. The solvent was removed in vacuo, water (50 ml) added and the product extracted into ethyl acetate (3×50 ml). The combined organics were washed with water (50 ml), concentrated brine (50 ml), dried over anhydrous sodium sulfate, filtered and concentrated in vacuo and the product purified by "flash" chromatography over silica gel to afford a colorless oil (63% yield). An ethanolic solution of the product was treated with 2 equivalents of 1N-HCl in diethyl ether to afford the HCl salt of the titled compound as a white solid.

Elemental Analysis for: C25H31N5O 2HCl Calculated: C, 61.22; H, 6.78; N, 14.28 Found: C, 61.28; H, 6.87; N, 14.33

Compounds of the present invention bind with very high affinity to the 5-HT1A receptor and consequently, they are useful for the treatment of central nervous system disorders such as depression, anxiety, sleep disorders, sexual dysfunction, alcohol and cocaine addiction, cognition enhancement and related problems in addition to the treatment of Alzheimer's disease, Parkinson's disease, obesity and migraine.

5-HT1A Receptor Binding Assay

High affinity for the serotonin 5—HT$_{1A}$ receptor was established by testing the claimed compound's ability to displace [$^3$]8-OH-DPAT binding in CHO cells stably transfected with human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

| Compound | 5-HT1A binding Ki (nM) |
| --- | --- |
| Example 9 | 4.72 |
| Example 10 | 7.1 |
| Example 11 | 0.88 |

Hence, compounds of the present invention exhibit high affinity for the 5HT1A receptor subtype. Accordingly, compounds of the present invention are useful for treatment of disorders of the central nervous system associated with 5HT1A receptor subtype and may be administered to a patient suffering from one or more of said disorders. Treatment, as used herein, refers to the alleviation or amelioration of symptoms of a particular disorder in a patient. In addition, compounds of the present invention may be administered as part of a treatment regime that includes other agents which act on the central nervous system. In some preferred embodiments, compounds of the present invention are part of a combination therapy including a serotonin reuptake inhibitor. Serotonin reuptake inhibitors useful in combination therapies of the present invention fluoxetine, fluvoxamine, paroxetine, sertraline and venlafaxine. Said agents may be administered at the same time, where they may be combined into a single dosage form, or at a different time, as compounds of the present invention, while still being part of the regime of the combination therapy.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of Formula 1 and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1 –100 mg/Kg for parenteral application, preferably 0.5–50 mg/Kg.

What is claimed is:

1. A compound according to Formula 1

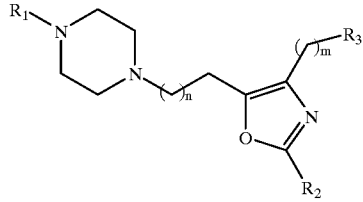 (1)

in which:

R₁ is aryl or heteroaryl;

R₂ is alkyl, alkylcycloalkyl, cycloalkyl, aryl, alkylaryl, heteroaryl, alkylheteroaryl, heterocycloalkyl, or alkylheterocycloalkyl; provided that the point of attachment is a carbon atom;

R3 is alkyl, alkylcycloalkyl, cycloalkyl, aryl, alkylaryl, heteroaryl, alkylheteroaryl, heterocycloalkyl or alkylheterocycloalkyl;

wherein heteroaryl is pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl, benzopyranyl and benzodioxanyl; n is 0 or 1 and m is an integer from 1 to 3; or a pharmaceutical salt thereof.

2. A compound of claim 1 which is 1-(4-benzyl-2-cyclohexyl-oxazol-5- ylmethyl)-4-(2,3-dihydro-benzo[1,4]dioxin-5-yl)-piperazine.

3. A compound of claim 1 which is 4-[4-(4-benzyl-2-cyclohexyl-oxazol-5- ylmethyl)-piperazin-1-yl]-1H-indole.

4. A compound of claim 1 which is 1-(4-benzyl-2-cyclohexyl-oxazol-5- ylmethyl)-4-(2-methoxyphenyl)-piperazine.

5. A compound of claim 1 which is 1-(4-benzyl-2-tert-butyl-oxazol-5-ylmethyl)-4-(2-methoxyphenyl)-piperazine.

6. A compound of claim 1 which is 4-[4-(4-benzyl-2-tert-butyl-oxazol-5-ylmethyl)-piperazin-1-yl]-1H-indole.

7. A compound of claim 1 which is 1-(4-benzyl-2-tert-butyl-oxazol-5-ylmethyl)-4-(2,3-dihydro-benzo[1,4]dioxin-5-yl)-piperazine.

8. A compound of claim 1 which is 1-(4-benzyl-2-cyclohexylmethyl-oxazol-5-ylmethyl)-4-(2-methoxyphenyl)-piperazine.

9. A compound of claim 1 which is 4-[4-(4-benzyl-2-cyclohexylmethyl-oxazol-5-ylmethyl) piperazin-1-yl]-1H-indole.

10. A compound of claim 1 which is 1-(4-benzyl-2-phenyl-oxazol-5-ylmethyl)-4-(2-methoxyphenyl)-piperazine.

11. A compound of claim 1 which is 1-(2-cyclohexyl-4-{(2-naphthyl)methyl}-oxazol-5-ylmethyl)-4-(2-methoxyphenyl)-piperazine.

12. A compound of claim 1 which is 1-(2-cyclohexyl-4-(4-fluorobenzyl)-oxazol-5-yl methyl)-4-(2-methoxyphenyl)-piperazine.

13. A compound of claim 1 which is 1-(4-benzyl-2-cyclohexylmethyl-oxazol-5-ylmethyl)-4-(2-fluorophenyl)-piperazine.

14. A compound of claim 1 which is 1-(4-benzyl-2-cyclohexyl-oxazol-5-ylmethyl)-4-(2-pyrimidyl)-piperazine.

15. A pharmaceutical composition comprising a compound according to Formula 1

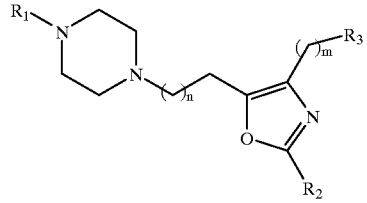 (1)

in which:

R₁ is aryl or heteroaryl;

R₂ is alkyl, alkylcycloalkyl, cycloalkyl, aryl, alkylaryl, heteroaryl, alkylheteroaryl, heterocycloalkyl, or alkylheterocycloalkyl; provided that the point of attachment is a carbon atom;

R3 is alkyl, alkylcycloalkyl, cycloalkyl, aryl, alkylaryl, heteroaryl, alkylheteroaryl, heterocycloalkyl or alkylheterocycloalkyl;

wherein heteroaryl is pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl, benzopyranyl and benzodioxanyl;

n is 0 or 1 and m is an integer from 1 to 3; or a pharmaceutical salt thereof, and a pharmaceutically acceptable carrier or excipient.

16. A method of treating a patient suffering from a disorder of the central nervous system associated with the 5-hydroxytryptamine-1A subtype comprising administering to said patient a therapeutically effective amount of a compound of Formula (1),

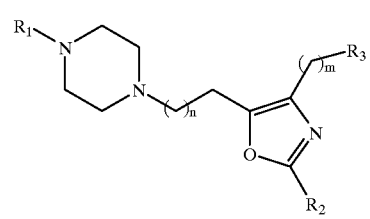 (1)

in which:

R₁ is aryl or heteroaryl;

R₂ is alkyl, alkylcycloalkyl, cycloalkyl, aryl, alkylaryl, heteroaryl, alkylheteroaryl, heterocycloalkyl, or alkylheterocycloalkyl; provided that the point of attachment is a carbon atom;

R3 is alkyl, alkylcycloalkyl, cycloalkyl, aryl, alkylaryl, heteroaryl, alkylheteroaryl, heterocycloalkyl or alkylheterocycloalkyl;

wherein heteroaryl is pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl, benzopyranyl and benzodioxanyl;

n is 0 or 1 and m is an integer from 1 to 3; or a pharmaceutical salt thereof.

17. The method of claim 16 wherein the disorder is depression, anxiety or panic.

18. The method of claim 16 wherein the disorder is sleep disorder or sexual dysfunction.

19. The method of claim 16 wherein the disorder is drug or alcohol addiction.

20. The method of claim 16 wherein the disorder is a cognitive disorder.

21. The method of claim 16 wherein the disorder is a neurodegenerative disease.

22. The method of claim 21 wherein the neurodegenerative diseases is Parkinson's disease or Alzheimer's disease.

23. The method of claim 16 wherein the disorder is migraine.

24. The method of claim 16 wherein the disorder is obesity.

25. The method of claim 16 further comprising administration of a serotonin reuptake inhibitor.

26. The method of claim 25 wherein the serotonin reuptake inhibitor is selected from the group consising of fluoxetine, fluvoxamine, paroxetine, sertraline and venlafaxine.

* * * * *